(12) United States Patent
Dlubala et al.

(10) Patent No.: US 8,440,634 B2
(45) Date of Patent: May 14, 2013

(54) BICYCLIC DERIVATIVES OF MORPHINE-6-GLUCURONIDE, PREPARATION METHOD THEREOF AND USE OF SAME IN THERAPEUTICS

(75) Inventors: Alain Dlubala, Paris (FR); Claire Trecant, Strasbourg (FR); Isabelle Ripoche, Aubiere Cedex (FR)

(73) Assignee: Sanofi, Paris (FR)

( * ) Notice: Subject to any disclaimer, the term of this patent is extended or adjusted under 35 U.S.C. 154(b) by 54 days.

(21) Appl. No.: 13/155,727

(22) Filed: Jun. 8, 2011

(65) Prior Publication Data

US 2011/0275580 A1 Nov. 10, 2011

Related U.S. Application Data

(63) Continuation of application No. PCT/FR2009/052446, filed on Dec. 8, 2009.

(30) Foreign Application Priority Data

Dec. 11, 2008 (FR) ..................... 08 06974

(51) Int. Cl.
| | |
|---|---|
| *A01N 43/04* | (2006.01) |
| *A01N 43/42* | (2006.01) |
| *A61K 31/70* | (2006.01) |
| *A61K 31/44* | (2006.01) |
| *C07D 489/00* | (2006.01) |
| *C07H 15/00* | (2006.01) |
| *C07H 17/00* | (2006.01) |
| *C07H 17/02* | (2006.01) |

(52) U.S. Cl.
USPC ........... 514/33; 514/282; 536/17.3; 536/17.4; 536/17.9; 536/18.1; 546/44

(58) Field of Classification Search .................. None
See application file for complete search history.

(56) References Cited

U.S. PATENT DOCUMENTS

| | | | |
|---|---|---|---|
| 3,766,188 A | 10/1973 | Murakami et al. | |
| 7,365,055 B2 * | 4/2008 | Temsamani et al. | ............ 514/27 |
| 2007/0116665 A1 | 5/2007 | Temsamani et al. | |

FOREIGN PATENT DOCUMENTS

| | | |
|---|---|---|
| FR | 2864082 | 6/2005 |
| WO | WO 93/03051 | 2/1993 |
| WO | WO 95/05831 | 3/1995 |
| WO | WO 98/46618 | 10/1998 |
| WO | WO 99/64430 | 12/1999 |
| WO | WO 2005/063263 | 7/2005 |

OTHER PUBLICATIONS

Hu et al., Acta Anaesthesiol Sin. Dec. 2000;38(4): abstract.*
U.S. Appl. No. 13/155,655, filed Jun. 8, 2011, Dlubala, et al.
U.S. Appl. No. 13/155,646, filed Jun. 8, 2011, Dlubala, et al.
Yoshimura, H., et al., Metabolism of Drugs. LX. 1) The synthesis of Codeine and Morphine Glucoronides 2), Chem. Pharm. Bull., vol. 16, No. 11, pp. 2114-2119, (1968).
Abdel-Monem, M. M., et al., N-Demethylation of Morphine and Structurally Related Compounds With Chloroformate Esters, Journal of Medicinal Chemistry, vol. 15, No. 2, (1972), pp. 208-210.
Auterhoff, et al., Die Farbreaktion des Morphines Nach E. Marquis, Archiv Der Pharmazie (Weinheim), vol. 306, No. 11, (1973), pp. 866-872.
Berrang, B., et al., Synthesis of Morphine-3,6-di-B-D-Glucuronide, Synthesis, (1997), pp. 1165-1168.
Brown, R. T., et al., A Simple Synthesis of Morphine-3,6-di-B-D-Glucuronide, Tetrahedron, vol. 56, (2000), pp. 7591-7594.
Cheng, G., et al., Syn Additions to 4a-Epoxypyranosides: Synthesis of L-Idopyranosides, Organic Letters, vol. 9, No. 23, pp. 4849-4852, (2007).
D'Amour et al., A Method for Determining Loss of Pain Sensation, Journal of Pharmacology and Exp. Ther., vol. 72, pp. 74-79, (1941).
Danishefsky, S. J., et al., A Stereoselective Totally Synthetic Route to Methyl a-Peracetylhikosaminide, J. Am. Chem. Soc., (1959), vol. 111, pp. 2193-2204.
Frances, B., et al., Further Evidence That Morphine-6B-Glucuronide is a More Potent Opioid Agonist Than Morphine, The Journal of Pharmacology and Experimental Therapeutics, vol. 262, No. 1, pp. 25-31, (1992).
Frensch, K., et al., Notiz Uber Oligoethylenglykolether des Morphins, Liebigs Ann. Chem. (1979), pp. 2118-2120.
McMillan, K. G., et al., Synthesis, Structure and Reactivity of 5-Pyranosyl-1,3,4-Oxathiazol-2-Ones, Carbohydrate Research, vol. 341, (2006), pp. 41-48.
Nakajima, R., et al., Synthesis of Methyl 1-O-(4-Hydroxymethamphetaminyl)-a-D-Glucopyranouronate, Chem. Pharm. Bull., vol. 53, No. 6, pp. 684-687, (2005).

(Continued)

*Primary Examiner* — Traviss C McIntosh, III
(74) *Attorney, Agent, or Firm* — Robert Kajubi; Ronald G. Ort

(57) ABSTRACT

The disclosure relates to compounds of formula (I):

(I)

wherein R1, R2, and n are as defined in the disclosure, and addition salts solvates and hydrates thereof. The disclosure also relates to the preparation method of said compounds and to the use of the same in therapeutics.

9 Claims, No Drawings

OTHER PUBLICATIONS

Narita, M., et al., Regulations of Opioid Dependence by Opioid Receptor Types, Pharmacology & Therapeutics, vol. 89, (2001), pp. 1-15.

Paul, D., et al., Pharmacological Characterization of Morphine-6B-Glucuronide, A Very Potent Morphine Metabolite, The Journal of Pharmacology and Experimental Therapeutics, (1989), vol. 251, pp. 477-483.

Vlahov, J., et al., Uber Eine Verbesserte Synthese Von B-Glucosiduronsaure-Derivaten, Liebigs Ann. Chem., (1983), pp. 570-574.

International Search Report for WO2010/067008 dated Jun. 17, 2010.

* cited by examiner

BICYCLIC DERIVATIVES OF MORPHINE-6-GLUCURONIDE, PREPARATION METHOD THEREOF AND USE OF SAME IN THERAPEUTICS

This application is a continuation of International application No. PCT/FR2009/052446, filed Dec. 8, 2009, which is incorporated herein by reference in its entirety; which claims the benefit of priority of French Patent Application No. 0806974, filed Dec. 11, 2008.

FIELD OF THE INVENTION

The present invention relates to bicyclic morphine-6-glucuronide derivatives, to their preparation and to their use for treating and preventing pain.

One subject of the present invention is compounds corresponding to formula (I)

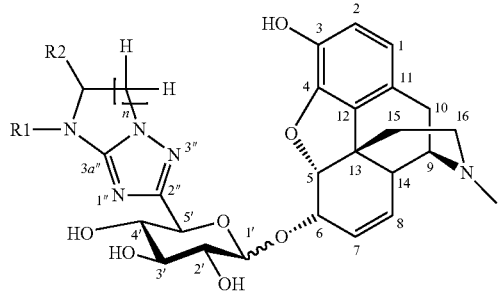

(I)

in which:
R1 represents a hydrogen atom or a group $(C_1\text{-}C_4)$alkyl,
R2 represents a hydroxyl group, a thiol group, a group $(C_1\text{-}C_4)$alkyloxy or a group thio$(C_1\text{-}C_4)$alkyl, and
n is an integer equal to 1 or 2,
in the form of base or of acid-addition salt, and also in the form of hydrate or solvate.

The compounds of formula (I) may comprise an asymmetric carbon. They may thus exist in the form of two enantiomers. These enantiomers, and also mixtures thereof, including racemic mixtures, form part of the invention.

The compounds of formula (I) comprise an anomeric carbon. They may exist in the form of α or β anomers. The α and β anomers, and also a mixture thereof, form part of the invention.

The compounds of formula (I) may exist in the form of bases or of acid-addition salts. Such addition salts form part of the invention.

These salts may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:
a group $(C_1\text{-}C_4)$alkyl: a substituted or unsubstituted, linear or branched, saturated aliphatic group, containing between 1 and 4 carbon atoms; examples that may be mentioned include methyl, ethyl, propyl, isopropyl, butyl, isobutyl and tert-butyl groups;
a hydroxyl group: a group —OH;
a thiol group: a group —SH;
a group $(C_1\text{-}C_4)$alkyloxy: a group —O—$(C_1\text{-}C_4)$alkyl in which the group $(C_1\text{-}C_4)$alkyl is as defined previously; examples that may be mentioned include methoxy, ethoxy, propoxy and butyloxy groups; and
a group thio$(C_1\text{-}C_4)$alkyl: a group —S—$(C_1\text{-}C_4)$alkyl in which the group $(C_1\text{-}C_4)$alkyl is as defined previously; examples that may be mentioned include thiomethyl, thioethyl, thiopropyl and thiobutyl groups.

Among the compounds of formula (I) according to the invention, a first group of compounds has one or more of the following characteristics:
R1 is a hydrogen atom,
R2 is a hydroxyl group, and
n is equal to 2.

Among the compounds of formula (I) according to the invention, mention may be made in particular of the following compound:
morphin-6-yl 5-C-(5-hydroxy-4,5,6,7-tetrahydro[1,2,4]triazolo[1,5-a]pyrimidin-2-yl)-β-D-xylopyranoside.

Preparation Process

In the text hereinbelow, the term "protecting group" means a group that can, firstly, protect a reactive function such as a hydroxyl or an amine during a synthesis and, secondly, regenerate the intact reactive function at the end of the synthesis. Examples of protecting groups and of protection and deprotection methods are given in "Protective Groups in Organic Synthesis", Greene et al., $2^{nd}$ Edition (John Wiley & Sons, Inc., New York).

In the text hereinbelow, the term "leaving group" means a group that may be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a methanesulfonate, benzenesulfonate, triflate, acetate, etc. Examples of leaving groups and references for preparing them are given in "Advances in Organic Chemistry", J. March, $3^{rd}$ Edition, Wiley Interscience, pp. 310-316.

Reaction Scheme 1 below illustrates the reaction for the particular example of morphin-6-yl 5-C-(5-hydroxy-4,5,6,7-tetrahydro[1,2,4]triazolo[1,5-a]pyrimidin-2-yl)-β-D-xylopyranoside.

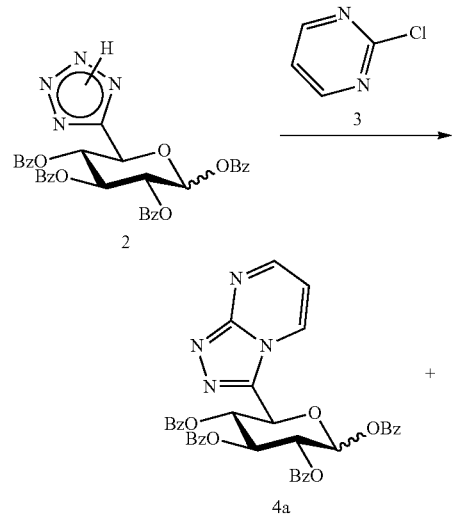

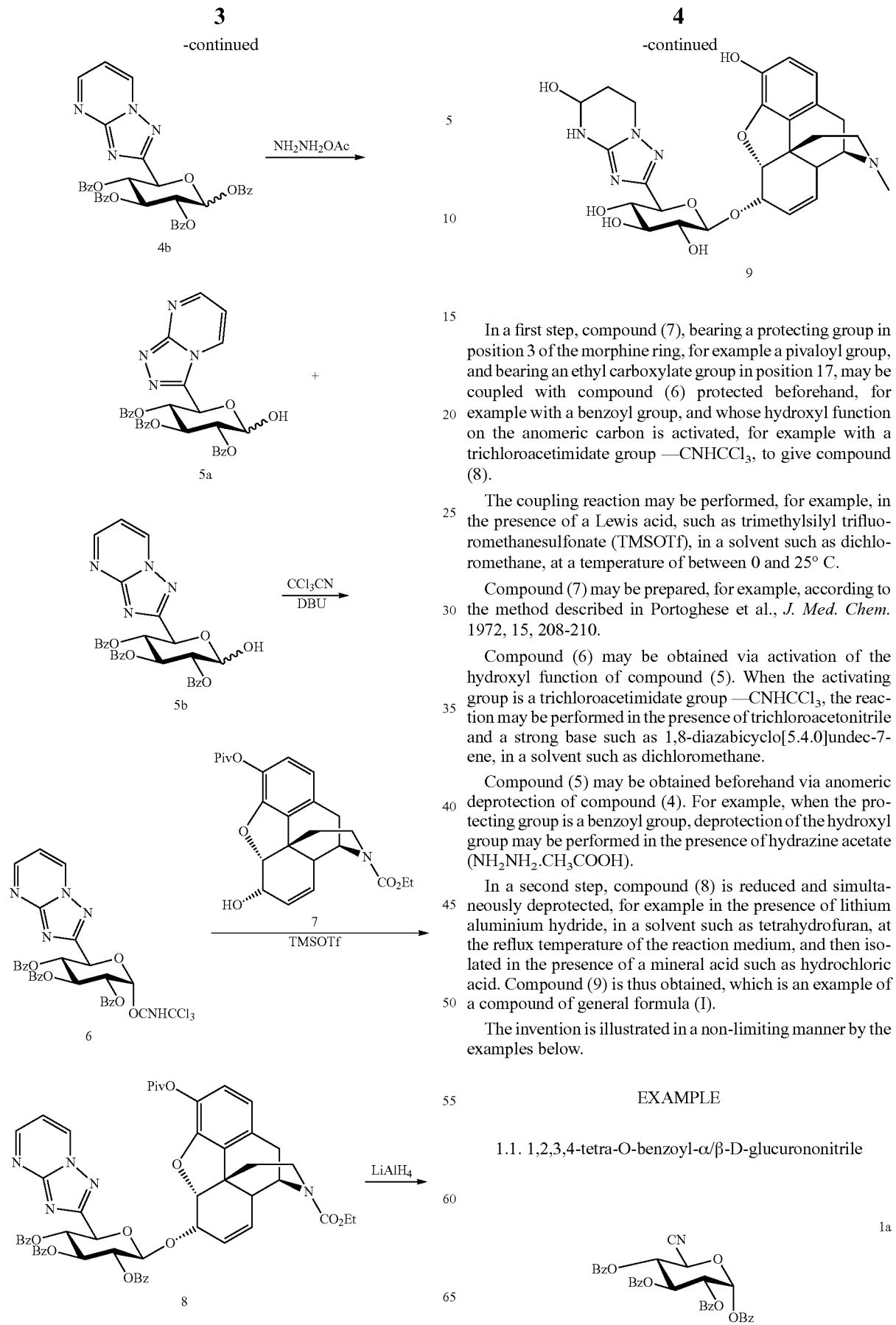

In a first step, compound (7), bearing a protecting group in position 3 of the morphine ring, for example a pivaloyl group, and bearing an ethyl carboxylate group in position 17, may be coupled with compound (6) protected beforehand, for example with a benzoyl group, and whose hydroxyl function on the anomeric carbon is activated, for example with a trichloroacetimidate group —CNHCCl$_3$, to give compound (8).

The coupling reaction may be performed, for example, in the presence of a Lewis acid, such as trimethylsilyl trifluoromethanesulfonate (TMSOTf), in a solvent such as dichloromethane, at a temperature of between 0 and 25° C.

Compound (7) may be prepared, for example, according to the method described in Portoghese et al., *J. Med. Chem.* 1972, 15, 208-210.

Compound (6) may be obtained via activation of the hydroxyl function of compound (5). When the activating group is a trichloroacetimidate group —CNHCCl$_3$, the reaction may be performed in the presence of trichloroacetonitrile and a strong base such as 1,8-diazabicyclo[5.4.0]undec-7-ene, in a solvent such as dichloromethane.

Compound (5) may be obtained beforehand via anomeric deprotection of compound (4). For example, when the protecting group is a benzoyl group, deprotection of the hydroxyl group may be performed in the presence of hydrazine acetate (NH$_2$NH$_2$.CH$_3$COOH).

In a second step, compound (8) is reduced and simultaneously deprotected, for example in the presence of lithium aluminium hydride, in a solvent such as tetrahydrofuran, at the reflux temperature of the reaction medium, and then isolated in the presence of a mineral acid such as hydrochloric acid. Compound (9) is thus obtained, which is an example of a compound of general formula (I).

The invention is illustrated in a non-limiting manner by the examples below.

EXAMPLE 1.1. 1,2,3,4-tetra-O-benzoyl-α/β-D-glucurononitrile

-continued

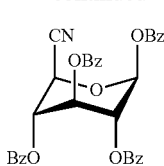
1b

To a suspension of D-glucuronamide (25.0 g, 0.129 mol) in pyridine (100 mL) at room temperature is added, over 30 minutes, a solution of benzoyl chloride (102 mL, 0.878 mol) in dichloromethane (90 mL). The reaction medium is stirred overnight at room temperature, and then dichloromethane (200 mL) and water (200 mL) are added. The organic phase is washed with 1N hydrochloric acid solution (200 mL), saturated sodium hydrogen carbonate solution (3×200 mL) and saturated sodium chloride solution (200 mL). The organic phase is dried over sodium sulfate and the solvent is removed under reduced pressure. The residue (yellow oil) is triturated in ethanol (200 mL) to give a mixture of anomers (43.4 g, 57%) in the form of pale yellow crystals. The proton NMR spectrum in deuteriochloroform, $CDCl_3$, shows an α/β ratio of 2/1.

Melting point: 209-212° C.

$^1$H NMR (400 MHz, $CDCl_3$): δ 8.10-7.30 (m, 20Hα+20H β, H-aro), 6.88 (d, 1Hα, J 3.5 Hz, H-1α), 6.57 (d, 1H β, J 3.0 Hz, H-1 β), 6.21 (t, 1Hα, J 9.5 Hz, H-3α), 5.93 (t, 1Hα, J 9.5 Hz, H-4α), 5.84 (t, 1H β, J 4.0 Hz, H-3 β), 5.71-5.65 (m, 1Hα+1H α, H-2α, H-4 β), 5.64 (m, 1H β, H-2 β), 5.16 (d, 1H β, J 4.0 Hz, H-5 β), 5.11 (d, 1Hα, J 9.5 Hz, H-5).

$^{13}$C NMR (100 MHz, $CDCl_3$): δ 165.5, 165.1, 164.8, 164.6, 164.3, 163.8 (C=O), 134.4-128.0 (C-aro), 115.3 (C-6 β), 114.1 (C-6α), 90.9 (C-1 β), 89.4 (C-1α), 69.3, 69.2, 69.0 (C-2 α, C-3 α, C-4 α), 67.4 (C-4 β), 66.7, 66.5 (C-2 β, C-3 β), 61.9 (C-5 α), 60.8 (C-5 β).

Mass calculated for $C_{34}H_{25}NO_9Na$ $[M+Na]^+$ 614.1427. Found 614.1422.

1.2. 1,2,3,4-tetra-O-benzoyl-5-C-(tetrazol-5-yl)-α/β-D-xylopyranose

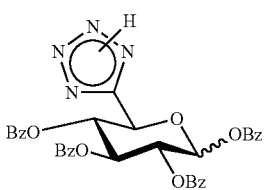
2

To a solution of 1,2,3,4-tetra-O-benzoyl-α/β-D-glucurononitrile prepared previously (43.0 g, 72.8 mmol) in toluene (500 mL) are added bis(tributyltin) oxide (3.70 mL, 7.26 mmol) and trimethylsilyl azide (28.7 mL, 216 mmol). The reaction medium is stirred overnight at reflux. The solvent is removed under reduced pressure and the residue is purified by chromatography on silica gel (1/1 to 0/1 cyclohexane/ethyl acetate) to give 1,2,3,4-tetra-O-benzoyl-5-C-(tetrazol-5-yl)-α/β-D-xylopyranose (27.0 g, 59%) in the form of brown crystals. The proton NMR spectrum in $CDCl_3$ shows an α/β ratio of 2/1.

Melting point 144-147° C.

$^1$H NMR (400 MHz, $CDCl_3$): δ 8.19-7.28 (m, 20Hα+20H β, H-aro), 7.06 (d, 1Hα, J 3.5 Hz, H-1α), 6.50-6.44 (m, 1H β+1Hα, H-1 β. H-3α), 6.21 (t, 1H β, J 9.0 Hz, H-3 β), 6.13-6.01 (m, 2H β+1Hα, H-4 β, H-4αH-2 β), 5.90-5.85 (m, 2Hα, H-2α, H-5α), 5.66 (d, 1H β, J 9.0 Hz, H-5 β).

$^{13}$C NMR (100 MHz, $CDCl_3$): δ 165.79, 165.2, 164.7 (C=O, C=N), 134.4-128.1 (C-aro), 93.0 (C-1 β), 89.9 (C-1α), 72.0, 70.5, 70.4, 70.3, 69.5 (C-2α, C-2 β, C-3α, C-3 β, C-4α, C-4 β), 68.9 (C-5 β), 67.0 (C-5α).

Mass calculated for $C_{34}H_{26}N_4O_9Na$ $[M+Na]^+$ 657.1597. Found 657.1595.

1.3. 1,2,3,4-tetra-O-benzoyl-5-C-([1,2,4]triazolo[4,3-a]pyrimidin-3-yl)-α/β-D-xylopyranose (4a)

1,2,3,4-tetra-O-benzoyl-5-C-([1,2,4]triazolo[1,5-a]pyrimidin-3-yl)-α/β-D-xylopyranose (4b)

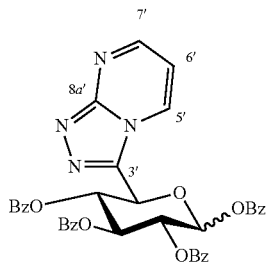
4a

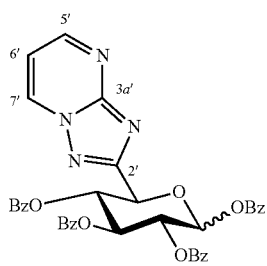
4b

A solution of 1,2,3,4-tetra-O-benzoyl-5-C-(tetrazol-5-yl)-α/β-D-xylopyranose (2) (3.0 g, 4.73 mmol) and 2-chloropyrimidine (813 mg, 7.10 mmol) in pyridine (38 mL) is maintained at reflux with stirring overnight.

The solvent is removed under reduced pressure and the residue is purified by chromatography on silica gel (3/7 cyclohexane/ethyl acetate) to give a mixture of the isomers 1,2,3,4-tetra-O-benzoyl-5-C-([1,2,4]triazolo[4,3-a]pyrimidin-3-yl)-α/β-D-xylopyranose (4a) (1.8 g) and 1,2,3,4-tetra-O-benzoyl-5-C-([1,2,4]triazolo[4,3-a]pyrimidin-3-yl)-α/β-D-xylopyranose (4b) (0.6 g) in the form of pale yellow crystals. The proton NMR spectrum in $CDCl_3$ shows an α:β ratio of 2/1 for the isomer 1,2,3,4-tetra-O-benzoyl-5-C-([1,2,4]triazolo[4,3-a]pyrimidin-3-yl)-α/β-D-xylopyranose (4a) and 7/3 for 1,2,3,4-tetra-O-benzoyl-5-C-([1,2,4]triazolo[1,5-a]pyrimidin-3-yl)-α/β-D-xylopyranose (4b).

The overall reaction yield is 74%.

Analyses for 1,2,3,4-tetra-O-benzoyl-5-C-([1,2,4] triazolo[4,3-a]pyrimidin-3-yl)-α/β-D-xylopyranose 4a Rf=0.55 (1/4 cyclohexane/ethyl acetate)
Melting point: 175-179° C.
$^1$H NMR (400 MHz, $CDCl_3$): δ 8.93 (m, 1Hα, H-5'α or H-7'α), 8.87 (m, 1Hβ, H-5'β or H-7'β), 8.73 (m, 1Hα, H-5'α or H-7'α), 8.64 (m, 1Hβ, H-5'β or H-7'β), 8.22-7.25 (m, 20Hα+20Hβ, H-aro), 7.04 (d, 1Hα, J 3.5 Hz, H-1α), 7.00 (dd, 1Hα, J 4.0 Hz, J 7.0 Hz, H-6'α), 6.93 (dd, 1Hβ, J 3.5 Hz, J 6.5 Hz, H-6'β), 6.57 (t, 1Hα, J 9.5 Hz, H-3α), 6.52 (d, 1Hβ, J 7.5 Hz, H-1β), 6.29 (m, 2Hβ, H-3β, H-4β), 6.11-6.01 (m, 2Hα+1Hβ, H-4α, H-5α, H-2β), 5.93 (dd, 1Hα, J 3.5 Hz, J 10.0 Hz, H-2α), 5.90-5.86 (m, 1Hβ, H-5β).

$^{13}$C NMR (100 MHz, CDCl$_3$): δ 165.5, 165.2, 165.1, (C=O), 164.6 (C-3'β), 164.4 (C-3'α), 155.1 (C-8a'α, C-8a'β), 154.2 (C-5'α or C-7'α), 154.0 (C-5'β or C-7'β), 140.3 (C-5'β or C-7'β), 140.1 (C-5'α or C-7'α), 134.4, 134.2, 133.8, 133.7, 133.5, 132.5, 132.4, 130.2-128.3 (C-aro), 110.4 (C-6'α, C-6'β), 93.0 (C-1β), 89.7 (C-1α), 71.5 (C-2β or C-3β or C-4β or C-5β), 70.6 (C-2β or C-3β or C-4β or C-5β), 70.4 (C-2β), 70.0 (C-2β or C-3β or C-4β or C-5β), 69.5 (C-3α or C-4α), 69.1 (C-3α or C-4α), 68.7 (C-5β).

Mass calculated for C$_{38}$H$_{29}$N$_4$O$_9$ [M+H]$^+$: 685.1935. Found 685.1953.

Analyses for 1,2,3,4-tetra-O-benzoyl-5-C-([1,2,4]triazolo[1,5-a]pyrimidin-3-yl)-α/β-D-xylopyranose 4b Rf=0.65 (1/4 cyclohexane/ethyl acetate)
Melting point: 188-190° C.

$^1$H NMR (400 MHz, CDCl$_3$): δ 8.80-8.71 (m, 2Hα+2Hβ, H-5'α, H-7'α, H-5'β, H-7'β), 8.22-7.30 (m, 20Hα+20Hβ, H-aro), 7.10 (dd, 1Hα, J 6.5 Hz, J 4.5 Hz, H-6'α), 7.07-7.02 (m, 1Hα+1Hβ, H-6'β, H-1α), 6.47 (m, 1Hα+1Hβ, H-1β+H-3α), 6.27-6.16 (m, 1Hα+2Hβ, H-4α, H-3β, H-4β), 6.06 (m, 1Hβ, H-2β), 5.89 (dd, 1Hα, J 3.5 Hz, J 10.0 Hz, H-2α), 5.73 (d, 1Hα, J 10.0 Hz, H-5α), 5.53 (d, 1Hβ, J 9.0 Hz, H-5β).

$^{13}$C NMR (100 MHz, CDCl$_3$): δ 165.8, 165.6, 165.3, 165.0, 164.8, 164.5, 164.2 (C=O), 164.0 (C-2'α), 163.8 (C-2'β), 155.3 (C-3a'α, C-3a'β), 155.1 (C-7'α), 155.0 (C-7'β), 136.0 (C-5'α, C-5'β), 134.0, 133.7, 133.4-133.2, 130.2-128.2 (C-aro), 110.7 (C-6'α), 110.6 (C-6'β), 92.9 (C-1β), 90.0 (C-1α), 72.5 (C-3β or C-4β or C-5β), 72.0 (C-3β or C-4β or C-5β), 71.3 (C-4α), 70.6 (C-3α), 70.3 (C-2α), 69.4 (C-5α).

Mass calculated for C$_{38}$H$_{29}$N$_4$O$_9$ [M+H]$^+$: 685.2524, found: 685.1953.

1.4. 2,3,4-tri-O-benzoyl-5-C-([1,2,4]triazolo[1,5-a]pyrimidin-2-yl)-α/β-D-xylopyranose (5b)

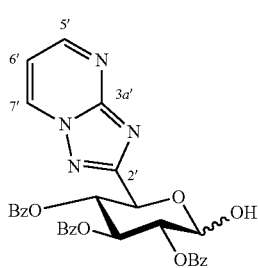

5b

To a solution of the compound 1,2,3,4-tetra-O-benzoyl-5-C-([1,2,4]triazolo[4,3-a]pyrimidin-3-yl)-α/β-D-xylopyranose (4a) or 1,2,3,4-tetra-O-benzoyl-5-C-([1,2,4]triazolo[1,5-a]pyrimidin-3-yl)-α/β-D-xylopyranose (4b) (500 mg, 0.73 mmol) in N,N-dimethylformamide (19 mL) at 0° C. is added hydrazine acetate (101 mg, 1.10 mmol) portionwise over 10 minutes. The reaction medium is stirred for 1 hour at 0° C. and then for 2 hours at room temperature.

The solvent is removed under reduced pressure and the residue is purified by chromatography on silica gel (1/4 cyclohexane/ethyl acetate) to give 2,3,4-tri-O-benzoyl-5-C-([1,2,4]triazolo[1,5-a]pyrimidin-2-yl)-α/β-D-xylopyranose 5 (284 mg, 67%) in the form of white crystals. The proton NMR spectrum in CDCl$_3$ shows an α:β ratio of 4/1.

Rf=0.30 (1/4 cyclohexane/ethyl acetate)
Melting point: 133-135° C.

$^1$H NMR (400 MHz, CDCl$_3$) for the α anomer: δ 8.77 (dd, 1H, J 2.0 Hz, J 7.0 Hz, H-5' or H-7'), 8.69 (m, 1H, H-5' or H-7'), 8.02-7.27 (m, 15H, H-aro), 7.04 (m, 1H, H-6'), 6.43 (t, 1H, J 10.0 Hz, H-3), 6.11 (t, 1H, J 10.0 Hz, H-4), 5.95 (d, 1H, J 3.5 Hz, H-1), 5.88 (d, 1H, J 10.0 Hz, H-5), 5.49 (dd, 1H, J 3.5 Hz, J 10.0 Hz, H-2).

$^{13}$C NMR (100 MHz, CDCl$_3$) for the α anomer: δ 165.8, 165.7, 165.0 (C=O), 164.9 (C-2'), 155.2 (C-3a'), 155.1 (C-7'), 136.1 (C-5'), 133.2-132.9, 129.3-128.2 (C-aro), 110.8 (C-6'), 90.8 (C-1), 72.2 (C-2), 71.7 (C-4), 70.5 (C-3), 66.3 (C-5).

Mass calculated for O$_{31}$H$_{25}$N$_4$O$_8$ [M+H]$^+$: 581.1672. Found 581.1661.

1.5. 2,3,4-tri-O-benzoyl-5-C-([1,2,4]triazolo[1,5-a]pyrimidin-2-yl)-α-D-xylopyranosyl trichloroacetimidate (6)

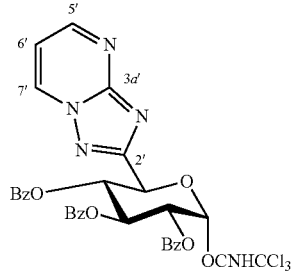

6

To a solution of 2,3,4-tri-O-benzoyl-5-C-([1,2,4]triazolo[1,5-a]pyrimidin-2-yl)-α/β-D-xylopyranose 5 (650 mg, 1.12 mmol) in dichloromethane (15 mL) at room temperature are added 1,8-diazobicyclo[5.4.0]undec-7-ene (186 μL, 1.24 mmol) and then trichloroacetonitrile (2.2 ml, 21.94 mmol). The reaction medium is stirred for 1.5 hours at room temperature. A solution of acetic acid (70 μL, 1.22 mmol) in water (7 mL) is added. The phases are separated, and the organic phase is washed with water (7 mL) and then dried over sodium sulfate.

The solvent is removed under reduced pressure and the residue is purified by chromatography on silica gel (silica neutralized beforehand by washing with a 5% solution of triethylamine in ethyl acetate) (1/1 cyclohexane/ethyl acetate) to give 2,3,4-tri-O-benzoyl-5-C-([1,2,4]triazolo[1,5-a]pyrimidin-2-yl)-α-D-xylopyranosyl trichloroacetimidate (6) (565 mg, 70%) in the form of yellow crystals.

Rf=0.35 (2/3 cyclohexane/ethyl acetate)
Melting point: 72-73° C.
$[α]^{25}_D$=117.2 (c=0.1, CDCl$_3$)

$^1$H NMR (400 MHz, CDCl$_3$): δ 8.81-8.76 (m, 2H, H-5', H-7'), 8.69 (s, 1H, NH), 8.00-7.29 (m, 15H, H-aro), 7.11 (dd, 1H, J 4.0 Hz, J 7.0 Hz, H-6'), 7.00 (d, 1H, J 3.5 Hz, H-1), 6.43

(t, 1H, J 10.0 Hz, H-3), 6.20 (t, 1H, J 10.0 Hz, H-4), 5.81 (dd, 1H, J 3.5 Hz, J 10.0 Hz, H-2), 5.71 (d, 1H, J 10.0 Hz, H-5).

$^{13}$C NMR (100 MHz, CDCl$_3$): δ 165.6, 165.3, 164.7 (C=O), 164.0 (C-2'), 160.4 (C=N), 155.4 (C-3a'), 155.1 (C-7'), 135.9 (C-5'), 133.5-133.2, 129.9-128.2 (C-aro), 110.7 (C-6'), 93.3 (C-1), 71.1 (C-4), 70.6 (C-2), 70.1 (C-3), 69.4 (C-5).

1.6. 3-O-pivaloyl-N-ethoxycarbonylnormorphin-6-yl 2,3,4-tri-O-benzoyl-5-C-([1,2,4]triazolo[1,5-a]pyrimidin-2-yl)-β-D-xylopyranoside (8)

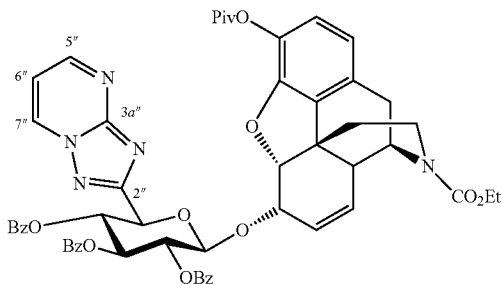

To a solution of 2,3,4-tri-O-benzoyl-5-C-([1,2,4]triazolo[1,5-a]pyrimidin-2-yl)-α-D-xylopyranosyl trichloroacetimidate (6) (1.5 g, 2.07 mmol) and 3-O-pivaloyl-N-ethoxycarbonylnormorphine (7) (738 mg, 1.73 mmol) in dichloromethane (24 mL) cooled to 0° C. is added trimethylsilyl trifluoromethanesulfonate (1.2 mL, 6.61 mmol). The reaction medium is stirred for 30 minutes at 0° C. and then for 1 hour at room temperature.

Hünig's base (1.1 mL) is added, and the mixture is stirred for 15 minutes and then concentrated to dryness under reduced pressure. The residue is purified by chromatography on silica gel (1/4 cyclohexane/ethyl acetate) to give the compound 3-O-pivaloyl-N-ethoxycarbonylnormorphin-6-yl 2,3,4-tri-O-benzoyl-5-C-([1,2,4]triazolo[1,5-a]pyrimidin-2-yl)-β-D-xylopyranoside (8) (470 mg, 31%) in the form of yellow crystals.

Rf=0.45 (1/4 cyclohexane/ethyl acetate)
Melting point: 171.5° C.
$[\alpha]^{25}_D$=−65.3 (c=0.5, CDCl$_3$)
$^1$H NMR (400 MHz, CDCl$_3$): δ 8.80 (dd, 1H, J 2.0 Hz, 4.0 Hz, H-5" or H-7"), 8.75 (dd, 1H, J 2.0 Hz, 7.0 Hz, H-5" or H-7"), 8.02-7.29 (m, 15H, H-aro), 7.10 (dd, 1H, J 4.0 Hz, J 7.0 Hz, H-6"), 6.71 (d, 1H, J 8.0 Hz, H-1), 6.52 (d, 1H, J 8.0 Hz, H-2), 6.21 (m, 1H, H-4'), 5.95 (t, 1H, J 9.0 Hz, H-3'), 5.75-5.69 (m, 2H, H-2', H-8), 5.47 (d, 1H, J 7.0 Hz, H-1'), 5.34 (d, 1H, J 9.5 Hz, H-5'), 5.23 (m, 1H, H-7), 4.98 (d, 1H, J 5.5 Hz, H-5), 4.93 (m, 1H, H-9), 4.46 (m, 1H, H-6), 4.20-4.05 (m, 2H, OCH$_2$CH$_3$), 3.99 (m, 1H, H-16a), 3.00 (m, 1H, H-16b), 2.90-2.70 (m, 2H, H-10), 2.48 (m, 1H, H-14), 1.88 (m, 2H, H-15), 1.31-1.25 (m, 12H, C(CH$_3$)$_3$, OCH$_2$CH$_3$).

$^{13}$C NMR (100 MHz, CDCl$_3$): δ 165.7, 165.2, 164.7 (C=O), 155.4 (C-3a"), 154.9 (C-7"), 136.0 (C-5"), 133.1-128.2 (C-aro), 122.2 (C-1), 119.2 (C-2), 110.6 (C-6"), 99.4 (C-1'), 89.9 (C-5), 73.0 (C-6), 72.7 (C-3'), 72.2 (C-2'), 71.3 (C-4', C-5'), 61.5 (OCH$_2$CH$_3$), 49.8 (C-9), 44.3 (C-13), 39.8 (C-14), 37.2 (C-16), 35.3 (C-15), 30.0 (C-10), 27.2 (C(CH$_3$)$_3$), 14.7 (OCH$_2$CH$_3$).

Mass calculated for C$_{55}$H$_{52}$N$_5$O$_{13}$ [M+H]$^+$: 990.356, found: 990.3596.

1.7. morphin-6-yl 5-C-(5-hydroxy-4,5,6,7-tetrahydro[1,2,4]triazolo[1,5-a]pyrimidin-2-yl)-β-D-xylopyranoside (9)

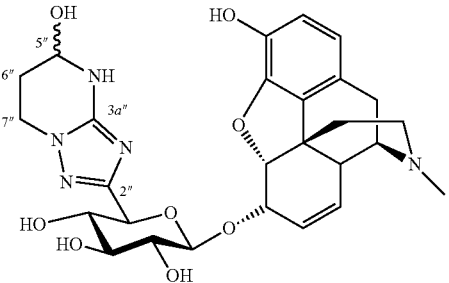

To a suspension of lithium aluminium hydride (140 mg, 3.69 mmol) in tetrahydrofuran (6 mL) is added a solution of the compound 3-O-pivaloyl-N-ethoxycarbonylnormorphin-6-yl 2,3,4-tri-O-benzoyl-5-C-([1,2,4]triazolo[1,5-a]pyrimidin-2-yl)-β-D-xylopyranoside (8) (250 mg, 0.28 mmol) in tetrahydrofuran (6 mL).

The reaction medium is stirred at reflux for 1 hour. Ethyl acetate is added to destroy the excess lithium aluminium hydride, and the medium is brought to pH 1 by adding 1N hydrochloric acid solution. The reaction medium is concentrated to dryness. The residue is purified a first time on a reverse-phase chromatography column (pure H$_2$O and then 80/20 (H$_2$O+1% trifluoroacetic acid)/acetonitrile) to remove the salts.

A second purification by reverse-phase preparative chromatography (95/5 to 20/80 gradient of (H$_2$O+0.1% trifluoroacetic acid)/acetonitrile) affords morphin-6-yl 5-C-(5-hydroxy-4,5,6,7-tetrahydro[1,2,4]triazolo[1,5-a]pyrimidin-2-yl)-β-D-xylopyranoside (9) in the form of white crystals (61 mg, 40%).

Melting point: 201° C.
$[\alpha]^{23}_D$=−118.4 (c=0.5, methanol)
$^1$H NMR (300 MHz, D$_2$O): 6.80 (d, 1H, J 8.0 Hz, H-1), 6.72 (d, 1H, J 8.0 Hz, H-2), 5.83 (m, 1H, H-8), 5.43 (m, 1H, H-7), 5.36 (m, 1H, H-5"), 5.29 (d, 1H, J 5.5 Hz, H-5), 4.91 (d, 1H, J 8.0 Hz, H-1'), 4.52 (m, 1H, H-6), 4.51 (d, 1H, J 9.5 Hz, H-5'), 4.32-4.20 (m, 2H, H-9, H-6"a), 4.10 (m, 1H, H-6"b), 3.78 (t, 1H, J 9.5 Hz, H-4'), 3.68 (t, 1H, J 9.5 Hz, H-3'), 3.53 (dd, 1H, J 8.0 Hz, J 9.5 Hz, H-2'), 3.40 (m, 1H, H-16a), 3.25 (m, 1H, H-10a), 3.12 (m, 1H, H-16b), 3.05-2.89 (m, 5H, H-10b, H-14, NCH$_3$), 2.35-2.11 (m, 4H, H-15, H-7").

$^{13}$C NMR (75 MHz, D$_2$O): 131.2 (C-8), 126.1 (C-7), 120.5 (C-2), 117.8 (C-1), 102.5 (C-1'), 88.3 (C-5), 74.9 (C-3'), 73.7 (C-6), 72.9 (C-2'), 71.7 (C-4'), 71.1 (C-5"), 70.4 (C-5'), 60.6 (C-9), 47.2 (C-16), 40.9 (NCH$_3$), 40.1 (C-6"), 38.5 (C-14), 32.4 (C-15), 26.2 (C-7"), 20.9 (C-10).

Mass calculated for C$_{27}$H$_{34}$N$_5$O$_8$ [M+H]$^+$: 556.2407, found: 556.3278.

Biological Activity

The compounds according to the invention underwent pharmacological trials to determine their analgesic effect.

Tests consisting in measuring the in vivo activity of the compounds of the invention on a nociceptive reflex response were performed. In this approach, the latency of the animal's nociceptive reflex response is measured as a pain indicator.

"Tail-Flick" Test

Procedure

The analgesic activity was determined by means of the "tail-flick" test in male Swiss mice (Iffa Credo). This test is based on the spontaneous nociceptive reflex of removal of the animal's tail caused by a painful heat stimulus (infrared source). The "tail-flick" test (D'Amour-Smith test, 1941, Pharmacol. Exp. Ther.; 72: 74-79) consists, after administering a product, in placing a mouse's tail at the focal point of the infrared source so as to produce a nociceptive heat stimulus (surface temperature of about 55-60° C.). The mouse's reaction time (RT) (latency between the moment when the light beam is switched on and the moment when the mouse removes its tail) was measured in duplicate at different times ranging from 20 minutes to 120 minutes after administration of the product. The heat intensity is regulated such that this removal reflex is between 0.5 and 3.5 seconds in the control animals, and arbitrarily represents the criterion for minimum analgesia (0%). Two reaction time measurements were taken before administration of the product for each mouse, to establish a baseline measurement time. A maximum time of 8 seconds was chosen as the maximum reaction time so as not to induce tissue damage by burning the animals, and arbitrarily represents the criterion for maximum analgesia (100%). The reaction time is increased by the analgesics relative to a control animal not receiving any treatment. The products were administered subcutaneously and orally at doses of between 1.25 and 30 mg/kg.

Results

The results obtained for the compounds of the invention are represented by the following data:
- the maximum percentage of analgesic activity (% MPE max index) obtained for each compound (at a test dose),
- the $ED_{50}$ (expressed in mg/kg) corresponding to the effective dose for each compound for which 50% analgesia was obtained; this is calculated at a given time after administration of the compounds; and
- the duration of the analgesic action at a given dose.

The percentage of analgesic activity (% MPE) is determined by the following formula:

$$\%MPE=(RTpost\text{-}administration-RTpre\text{-}administration)*100/(RTmax-RTpre\text{-}administration).$$

Among the most active compounds whose activity was evaluated subcutaneously, by way of example, morphin-6-yl 5-C-(5-hydroxy-4,5,6,7-tetrahydro-[1,2,4]triazolo[1,5-a]pyrimidin-2-yl)-β-D-xylopyranoside has a maximum percentage of analgesic activity (% MPE max index) of 80% for dose of 1.25 mg/kg and an $ED_{50}$ of less than 1.25 mg/kg determined 60 minutes after administration. The analgesic effects are persistent and last for more than 120 minutes via this administration route.

It is thus seen that the compounds according to the invention have analgesic activity.

The compounds according to the invention may thus be used for the preparation of medicaments, in particular medicaments intended for treating or preventing pain.

Thus, according to another of its aspects, a subject of the invention is medicaments comprising a compound of formula (I), or an addition salt thereof with a pharmaceutically acceptable acid, or alternatively a hydrate or a solvate.

These medicaments find their therapeutic use especially in the treatment and prevention of acute or chronic pain, especially peripheral pain or pain associated with inflammatory diseases such as arthritis, rheumatoid arthritis, osteoarthritis, spondylitis, gout, vasculitis, Crohn's disease and irritable bowel syndrome, neuropathic, muscular, bone, post-operative or migraine-related pain, lumbar pain, and cancer-related, diabetes-related or AIDS-related pain.

The compounds according to the invention also find their use, as analgesics, in the treatment of sexual dysfunctions and in particular in the treatment of male premature ejaculation.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a hydrate or a solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal, rectal or intraocular administration, the active principle of formula (I) above, or the possible salt, solvate or hydrate thereof, may be administered in a unit administration form, as a mixture with standard pharmaceutical excipients, to man and animals for the treatment of the above disorders or diseases.

The appropriate unit forms of administration include oral forms such as tablets, soft or hard gel capsules, powders, granules and oral solutions or suspensions, sublingual, buccal, intratracheal, intraocular, intranasal and inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating the pathologies indicated above, which comprises the administration to a patient of an effective dose of a compound according to the invention, or a pharmaceutically acceptable salt or hydrate or solvate thereof.

What is claimed is:

1. A compound of formula (I):

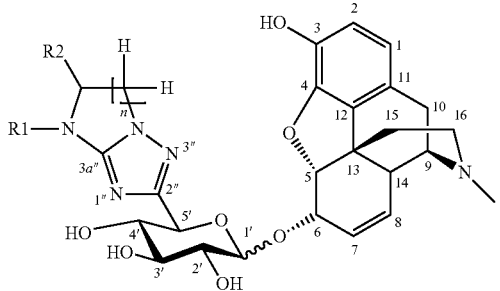

wherein:

R1 represents a hydrogen atom or a group $(C_1-C_4)$alkyl;

R2 represents a hydroxyl group, a thiol group, a group $(C_1-C_4)$alkyloxy or a group thio$(C_1-C_4)$alkyl; and n is an integer equal to 1 or 2;

or acid-addition salt, hydrate or solvate thereof.

2. The compound of formula (I) according to claim 1, wherein said compound has one or more of the following characteristics:

R1 is a hydrogen atom,

R2 is a hydroxyl group; and n is equal to 2;

or acid-addition salt, hydrate or solvate thereof.

3. The compound of formula (I) according to claim 1, wherein said compound is morphin-6-yl 5-C-(5-hydroxy-4,5,6,7-tetrahydro[1,2,4]triazolo[1,5-α]pyrimidin-2-yl)-β-D-xylopyranoside.

4. A pharmaceutical composition comprising a compound of formula (I) according to claim 1, or a pharmaceutically acceptable salt, a hydrate or a solvate of said compound, and one or more pharmaceutically acceptable excipient.

5. A pharmaceutical composition comprising a compound of formula (I) according to claim 2, or a pharmaceutically acceptable salt, a hydrate or a solvate of said compound, and one or more pharmaceutically acceptable excipient.

6. A pharmaceutical composition comprising a compound of formula (I) according to claim 3, or a pharmaceutically acceptable salt, a hydrate or a solvate of said compound, and one or more pharmaceutically acceptable excipient.

7. A method for treating in a patient comprising administering to said patient an effective dose of a compound of formula (I) according to claim 1 or a pharmaceutically acceptable salt or hydrate or solvate thereof.

8. A method for treating pain in a patient comprising administering to said patient an effective dose of a compound of formula (I) according to claim 2 or a pharmaceutically acceptable salt or hydrate or solvate thereof.

9. A method for treating pain in a patient comprising administering to said patient an effective dose of a compound of formula (I) according to claim 3 or a pharmaceutically acceptable salt or hydrate or solvate thereof.

* * * * *